United States Patent [19]

Ichikawa et al.

[11] Patent Number: 4,657,541
[45] Date of Patent: Apr. 14, 1987

[54] MEDICAL INSTRUMENT

[75] Inventors: Toshiji Ichikawa, Chofu; Yoshinori Ohachi, Fujinomiya, both of Japan

[73] Assignee: Terumo Kabushiki Kaisha, Tokyo, Japan

[21] Appl. No.: 741,000

[22] Filed: Jun. 4, 1985

[30] Foreign Application Priority Data

Jun. 7, 1984 [JP] Japan ............... 59-115401

[51] Int. Cl.$^4$ ............................................. A61B 19/00
[52] U.S. Cl. ............................ 604/408; 428/35; 428/36; 428/147; 604/266; 128/DIG. 24
[58] Field of Search ............... 128/DIG. 26; 604/262, 604/408, 266, 411, 317, 322, 332–345, 347, 349; 428/147, 327, 520; 206/524.8; 383/35

[56] References Cited

U.S. PATENT DOCUMENTS

| | | | |
|---|---|---|---|
| 2,655,453 | 10/1953 | Sandberg | 428/327 |
| 3,558,418 | 1/1971 | Porter et al. | 428/327 |
| 4,107,380 | 8/1978 | Wiesman | 428/520 |
| 4,257,422 | 3/1981 | Duncan | 604/266 |
| 4,286,597 | 9/1981 | Gajewski et al. | 604/408 |
| 4,300,559 | 11/1981 | Gajewski et al. | 604/262 |
| 4,478,961 | 10/1984 | Tanaka et al. | 604/266 |
| 4,490,420 | 12/1984 | Yoshida | 604/408 |
| 4,501,783 | 2/1985 | Hiragami et al. | 428/147 |
| 4,507,123 | 3/1985 | Yoshida | 604/408 |

OTHER PUBLICATIONS

Jahn, U.S. Def. Pub. T957,009, 4/5/77.

Primary Examiner—C. Fred Rosenbaum
Assistant Examiner—Jerome R. Smith, Jr.
Attorney, Agent, or Firm—Frishauf, Holtz, Goodman & Woodward

[57] ABSTRACT

A medical instrument formed of a wall of flexible vinyl chloride resin and enabled to be flattened is disclosed. In this instrument, the inner wall whose opposed surfaces come into mutual contact when the instrument is flattened is made of a flexible vinyl chloride resin composition containing cross-linked vinyl chloride resin particles and, therefore, enabled to form minute protuberances and depressions in the inner wall surfaces. This instrument is useful as bags for holding medical fluids and blood.

17 Claims, 5 Drawing Figures

4,657,541

MEDICAL INSTRUMENT

BACKGROUND OF THE INVENTION

1. Field of the Invention

This invention relates to a medical instrument. More particularly this invention relates to a medical instrument formed of a laminate of flexible vinyl chloride resin. This medical instrument has the inner wall thereof embossed to preclude the problem of blocking otherwise occurring between the opposed portions of the inner wall.

2. Description of the Prior Art

The flexible vinyl chloride resin enjoys outstanding processability, absolute physiological safety, high transparency, and inexpensiveness and, owing to these features, finds extensive utility in various medical instruments such as blood bags, transfusion bags, dialytic solution bags, and connection tubes.

In the medical instrument made of flexible vinyl chloride resin, however, owing to the migration of the plasticizer persisting in the flexible vinyl chloride resin, for example, the opposed portions of the inner walls of such instruments adhere to each other and induce the phenomenon of blocking. Consequently, these instruments have the possibility that their entrances will not readily open and their interiors will not readily admit medical preparations, blood, etc. Further in the case of tubular medical instrument, there is the possibility that their inner walls induce blocking of passage where they are bent.

As means of preventing the flexible vinyl chloride resin film from inducing the blocking, there is adopted, during the processing of the flexible vinyl chloride resin film, for example, a method whereby an embossing surface is formed on the backup roll incorporated in the sheet winding machine so as to impart protuberances on one surface of the sheet. This method has the disadvantage that the operation of this method necessitates use of an expensive embossing roll, the embossing surface of the roll is flattened by protracted use and, therefore, cannot continue to provide uniform embossing for a long time, and the method itself is not applicable to the inner surface of sheet in the inflation molding. There has also been proposed a method wherein a land portion near a die lip is cooled to differentiate the flow of resin on the outer surface and the inner surface of a film, induce convolution in the flow of resin and, as the result, corrugate the inner surface of the film and effect embossing of the surface (Japanese Patent Laid-Open No. SHO 50(1975)-55,679). Adoption of this method, however, adds to the number of restrictions imposed on the molding operation and degrades the capacity for mass-production. Moreover, the condition of embossing by this method is difficult to control and the embossing actually obtained lacks uniformity. A method which precludes the blocking by spraying of talc on the film surface and a method which avoids the blocking by having the flexible vinyl chloride resin incorporate therein in advance a lubricant such as stearic acid or palmitic acid thereby allowing the lubricant to imigrate to the surface of the film and impart activity thereto. The method which resorts to spray of talc entails deposition of talc as foreign matter on the film surface and, therefore, contamination of the fluid by the foreign matter, a fact which is detrimental to most purposes, let along medical treatment. The method which relies on the incorporation of a lubricant has the disadvantage that the lubricant will cause the phenomenon of blooming and the surface of flexible vinyl chloride resin film will be defiled with elapse of time.

As described above, none of the methods heretofore developed for the prevention of the flexible vinyl chloride resin film from the blocking proves fully effective as expected. Thus, the medical instruments made of flexible vinyl chloride resin are still used, with the problem of blocking pending solution.

An object of this invention, therefore, is to provide a novel medical instrument.

Another object of this invention is to provide a medical instrument, protected against the blocking due to adhesion between the opposed portions of the inner wall thereof.

Yet another object of this invention is to provide a medical instrument which is useful as a transfusion bag, a blood bag, a dialytic solution bag, and particularly a bag for CAPD medicine.

Still another object of this invention is to provide a medical instrument which will not induce the blocking even after sterilization by autoclaving.

A further object of this invention is to provide a medical instrument adapted so that the transparency of the apparatus will be increased by the presence of the fluid in the interior of the apparatus to a point where the fluid held therein can be visually observed from outside.

SUMMARY OF THE INVENTION

The objects described above are attained by a medical instrument formed of a wall of flexible vinyl chloride resin and, therefore, allowed to be flattened or collapsible, which apparatus is characterized by the fact that at least the inner wall of the instrument whose opposed surface come into mutual contact when the instrument is flattened is formed of a flexible vinyl chloride resin composition containing cross-linked vinyl chloride resin particles and, consequently, the surface of the inner wall is enabled to form minute protuberances and depressions therein.

This invention contemplates providing a medical instrument the outer wall of which is formed of a layer of flexible vinyl chloride resin containing cross-linked vinyl chloride resin particles in a concentration of less than 1.5% by weight. This invention also contemplates providing a medical instrument wherein the flexible vinyl chloride resin composition forming the inner wall of the apparatus contains the cross-linked vinyl chloride resin particles in a concentration in the range of 1.5 to 60% by weight, preferably 2 to 30% by weight, based on the total amount of vinyl chloride resin in the flexible vinyl chloride resin composition. This invention further contemplates providing a medical instrument wherein the cross-linked vinyl chloride resin particles are insoluble in tetrahydrofuran (THF). This invention contemplates providing a medical instrument wherein the cross-linked vinyl chloride resin particles have an average particle diameter in the range of 0.5 to 150 $\mu$m. Then, the present invention contemplates providing a medical instrument wherein the inner wall has a thickness in the range of about 50 to 500 $\mu$m, the outer wall has a thickness in the range of about 50 to 500 $\mu$m, and the ratio of the thickness of the inner wall to that of the outer wall is in the range of 1:1 to 1:10. Further, the present invention contemplates providing a medical instrument wherein the average height of minute protuberances and depressions in the inner wall surface is in the range of 1 to 45 μm. This invention further contemplates providing a medical instrument wherein fine protuberances and depressions are also formed in the surface of the outer wall. The present invention also contemplates providing a medical instrument wherein the outer wall contain cross-linked vinyl chloride particles in a concentration of not less than 0.01% by weight and less than 1.5% by weight.

DESCRIPTION OF THE PREFERRED EMBODIMENT

Figures 1, 3, 4:
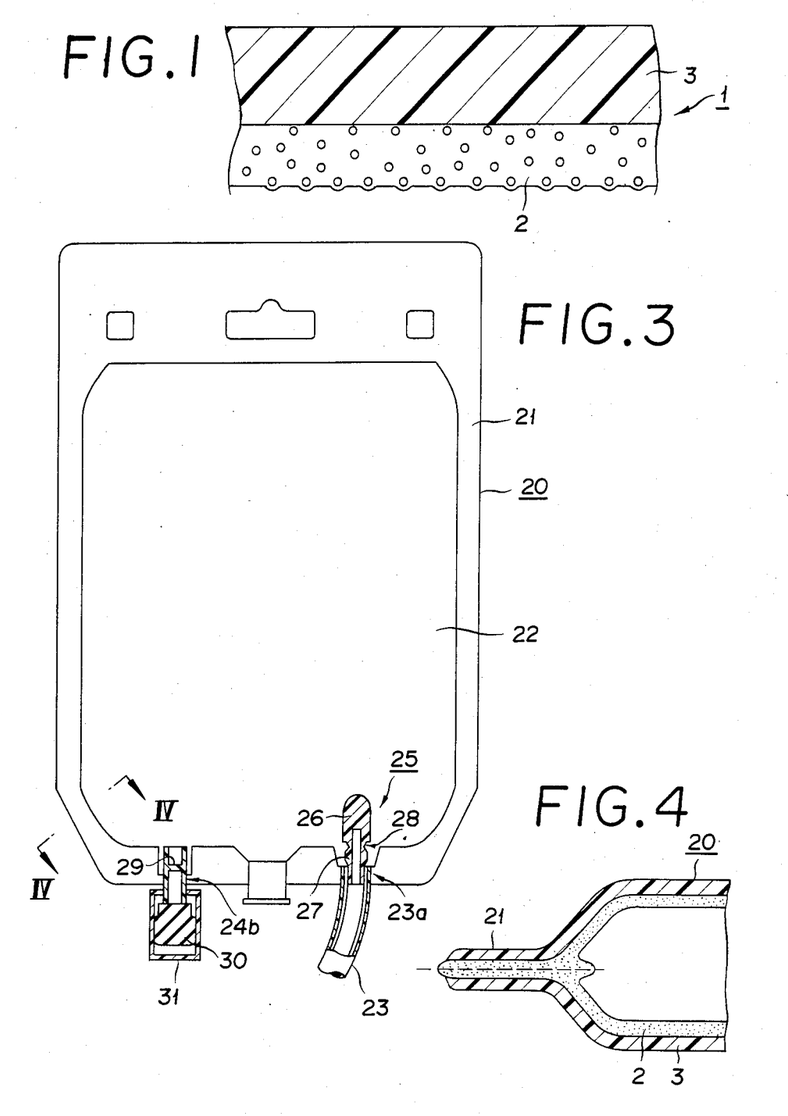
FIG. 1 is a longitudinal cross sectional view of a typical flexible vinyl chloride resin laminate used in a medical instrument embodying the present invention.
FIG. 3 is a partially sectioned front view of CAPD bag as one embodiment of the present invention.
FIG. 4 is an enlarged cross sectional view taken through FIG. 3 along the line IV—IV.

The medical instrument provided by this invention is formed of a laminate of flexible vinyl chloride resin. It is generally composed of two layers, i.e. an inner wall 2 of embossed surface and an outer layer 3 of flat smooth surface as illustrated in FIG. 1. Of course, it may additionally possess one or more intermediate layers.

The flexible vinyl chloride resin composition which forms the inner wall 2 of the medical instrument of the present invention contains cross-linked vinyl chloride resin particles.

The cross-linked vinyl chloride resin particles are composed of vinyl chloride monomer and/or a comonomer copolymerizable therewith and a polyfunctional compound containing at least two ethylenic double bonds in the molecular unit thereof. They are insoluble in tetrahydrofuran which is a good solvent for uncross-linked vinyl chloride resin. Examples of the comonomer copolymerizable with the vinyl chloride monomer include vinylidene chloride, ethylene, propylene, vinyl acetate, vinyl fluoride, styrene, vinyl toluene, vinyl pyridine, alkyl acrylates (such as methyl acrylate, ethyl acrylate, isopropyl acrylate, n-buyl acrylate, and 2-ethylhexyl acrylate), and alkyl methacrylates (such as methyl methacrylate, ethyl methacrylate, and 2-ethylhexyl methacrylate). Examples of the polyfunctional compound include diallyl compounds such as diallyl maleate and diallyl phthalate, diacrylate compounds such as ethylene glycol diacrylate, polyethylene glycol diacrylate, and bis-phenol A-modified diacrylate, dimethacrylate compounds such as ethylene glycol dimethacrylate and polyethylene glycol dimethacrylate, and 1,2-polybutadiene type compounds such as terminal hydroxyl group-1,2-polybutadiene and epoxidized 1,2-polybutadiene.

The cross-linked vinyl chloride resin particles to be used in the present invention are commercially available in the form of partially cross-linked vinyl chloride resin containing cross-linked vinyl chloride resin particles insoluble in THF in a concentration in the range of 5 to 90%, preferably 10 to 60%. Typical examples of the partially cross-linked vinyl chloride resin are products of Kanegafuchi Chemical Industry Co., Ltd. marketed under designations of XEL-A, XEL-B, XEL-C, XEL-D, and XEL-E, products of Chisso Corporation. marketed under designations of $SD_{7E}$, $SD_{10E}$, $SD_{13E}$, $CD_{18}$, $CD_{18K}$, $CD_{21}$, $CD_{21K}$, $CD_{25}$, and $CD_{25K}$, products of Shin-etsu Chemical Industry Co., Ltd. marketed under designations of GR-800S, GR-1300, GR-1300S, and GR-2500S, and products of Mitsui Toatsu Chemicals Co., Ltd. marketed under trademark designations of Vinycron DR-M and Vinycron DR-M-3.

The partially cross-linked vinyl chloride resin known to the art as described above can be used as incorporated in the flexible vinyl chloride resin composition forming the inner wall 2 of the medical instrument of the present invention, preferably also in the outer wall 3. The partially cross-linked is desired to possess a tetrahydrofuran-insoluble content of 5 to 90%, preferably 10 to 60%. The reason for this range is that the medical instrument produced by molding has the possibility of sustaining fish-eyes and other similar defects in outward appearance when the tetrahydrofuran-insoluble content exceeds 90% and the desired prevention of the inner surface of the apparatus from the blocking is not obtained satisfactorily when the tetrahydrofuran-insoluble content is less than 5%. The average particle diameter of the cross-linked vinyl chloride resin particles has bearing upon the effect in the prevention of the blocking. The prevention of the blocking is attained most effectively when the cross-linked vinyl chloride resin particles to be used possess an average particle diameter in the range of 0.5 to 150 μm, preferably 1 to 100 μm. The particle diameter and the shape of the cross-linked vinyl chloride resin particles are only required to be such that the particles as incorporated in the wall are enabled to give rise to the desired embossed surface. Thus, they are not particularly specified except that they should fulfil the purpose mentioned above.

During the preparation of the flexible vinyl chloride resin composition to form the inner wall 2, the partially cross-linked vinyl chloride resin of the foregoing description is incorporated generally in the range of 2 to 100% by weight, preferably 3 to 50% by weight, based on the total amount of vinyl chloride resin, though variable somewhat with the tetrahydrofuran-insoluble content thereof. The uncross-linked vinyl chloride resin particles contained in the aforementioned partially cross-linked vinyl chloride resin are melted during the manufacture of the apparatus. In the meantime, the cross-linked vinyl chloride resin particles contained in the partially cross-linked vinyl chloride resin remain intact within the inner wall 2. As the result, the inner wall 2 acquires a surface containing protuberances and depressions. In the flexible vinyl chloride resin composition to form the inner wall 2, the cross-linked vinyl chloride resin particles are contained in a concentration falling in the range of 1.5 to 60% by weight, preferably 2 to 30% by weight, based on the total amount of vinyl chloride resin. The term "total amount of vinyl chloride resin" as used herein refers to the total amount of the cross-linked vinyl chloride resin particles and the uncross-linked vinyl chloride resin in the flexible vinyl chloride resin composition forming the inner wall 2.

In the flexible vinyl chloride resin composition forming the inner wall 2 of the medical instrument, a plasticizer, uncross-linked vinyl chloride resin, and other additives may be incorporated, though not particularly specified, in addition to the cross-linked vinyl chloride resin particles.

Examples of the uncross-linked vinyl chloride resin which can be incorporated in the flexible vinyl chloride resin composition to form the inner wall 2 of the medical instrument of the present invention include homopolymer of vinyl chloride, polyvinylidene chloride, and copolymers of at least 50% by weight, more desirably at least 60% by weight, and most desirably at least 80% by weight, of vinyl chloride with other comonomer copolymerizable therewith. The average polymerization degree of the uncross-linked vinyl chloride resin falls in the range of 700 to 3,000, preferably 1,000 to 2,000. Examples of the comonomer usable with vinyl chloride include vinylidene chloride, ethylene, propylene, vinyl acetate, vinyl fluoride, styrene, vinyl toluene, vinyl pyridine, alkyl acrylates (such as methyl acrylate, ethyl acrylate, isopropyl acrylate, n-butyl acrylate, and 2-ethylhexyl acrylate), and alkyl methacrylates (such as methyl methacrylate, ethyl methacrylate, and 2-ethylhexylmethacrylate). The uncross-linked vinyl chloride resin is incorporated in a concentration of 98.5 to 40% by weight, preferably 98 to 70% by weight, based on the total amount of vinyl chloride resin in the flexible vinyl chloride resin composition to form the inner wall 2.

The plasticizer which may be additionally incorporated in the flexible vinyl chloride resin composition to form the inner wall 2 of the medical instrument of the present invention may be selected from among the plasticizers generally adopted for use in vinyl chloride resin. Typical examples of the plasticizer include phthalic esters such as dihexyl phthalate (DHP), di-2-ethylhexyl phthalate (DOP), di-n-octyl phthalate (DnOP), diisooctyl phthalate (DIOP), diheptyl phthalate, didecyl phthalate (DDP), diisodecyl phthalate (DIDP), and octyldecyl phthalate, trimellitic esters such as tributyl trimellitate and trioctyl trimellitate, alliphatic polybasic esters such as diotcyl adipate (DOA), dioctyl azelate (DOZ), and dioctyl sebacate (DOS), and citric esters such as tributyl acetyl citrate, trioctyl acetyl citrate, and tributyl citrate, preferably dialkyl phthalates (each alkyl group having 6 to 13 carbon atoms). When the number of carbon atoms in the alkyl group of the compound is less than 6, the plasticizer poses a problem in terms of safety. When this number exceeds 13, the plasticizer exhibits poor miscibility to the vinyl chloride resin. The alkyl group is desired to be of a straight chain form from the standpoint of safety. The two alkyl groups in the ester are not required to be identical with each other. The ester may be the product involving a mixture of two alcohols of different chain lengths.

The plasticizer is incorporated in an amount falling in the range of 20 to 100 parts by weight, preferably 30 to 70 parts by weight, based on 100 parts by weight of the total amount of the flexible vinyl chloride resin to form the inner wall 2.

Examples of the additives which may be incorporated in the flexible vinyl chloride resin composition to form the inner wall 2 include metallic soaps of calcium, zinc, etc. with stearic acid, lauric acid, ricinolic acid, naphthenic acid, etc., expoxidized vegetable oils such as epoxidized soybean oil and epoxidized linseed oil, lubricants, and other antioxidants. As the plasticizer, any of the heretofore known platicizers formed of high molecular polymers such as, for example, thermoplastic polyurethane resin can be used by the technique of polymer blend.

On the other hand, the outer wall 3 of the medical instrument of the present invention is formed of a layer generally made solely of uncross-linked flexible vinyl chloride resin or of a mixture of this resin with less than 0.5% by weight of cross-linked vinyl chloride resin. When the outer wall is formed of a layer made solely of the uncross-linked flexible vinyl chloride resin, it acquires a specular surface and, while the apparatus is holding the fluid therein, exhibits outstanding transparency. This outer wall nevertheless has the disadvantage that, during the molding of a sheet as the raw material for the outer wall, the sheet adheres to the roller so fast that it will not separate easily from the roller and will consequently impair the efficiency of molding work and, during the storge or transportation of the produced apparatus, the outer wall adheres to the adjoining apparatus, and the surface of the outer wall gives less pleasant sensation to the touch than a surface of satin finish. When the outer wall is formed of a layer made of a mixture of flexible vinyl chloride resin with less than 1.5% by weight of a cross-linked vinyl chloride resin, the surface of the outer wall enjoys sufficient smoothness and freedom from unwanted adhesion to the adjoining apparatus and suffers only minimally from random reflection of light and, while the apparatus is holding the fluid held therein, exhibits transparency so high as to enable the fluid held therein to be easily discerned. Desirably, therefore, the outer wall 3 is formed of a layer made of a mixture of flexible vinyl chloride resin with less than 1.5% by weight, preferably not less than 0.05% by weight and less than 1.5% by weight, of cross-linked vinyl chloride resin.

The aforementioned flexible vinyl chloride resin may be selected without any restriction from amount flexible vinyl chloride resin of all grades known to the art. It may be flexible vinyl chloride resin which is composed of 100 parts by weight of vinyl chloride resin, 20 to 80 parts by weight of plasticizer, and suitable amounts of other additives. Examples of the vinyl chloride resin, plasticizer, and other additives which can be incorporated in the aforementioned flexible vinyl chloride resin are the same as those of uncross-linked vinyl chloride resin, plasticizer, and other additives enumerated above as incorporable in the flexible vinyl chloride resin composition to form the inner wall 2. The cross-linked vinyl chloride resin particles to be added to the flexible vinyl chloride resin are the same as the cross-linked vinyl chloride resin particles described above as usable in the formation of the inner wall 2.

Figure 2:
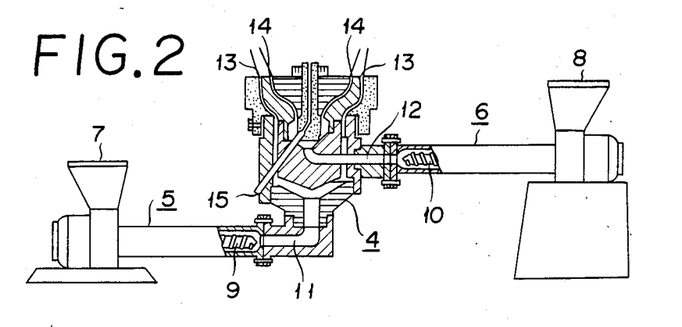
FIG. 2 is a longitudinal cross sectional view of an inflation molding system for production of the medical instrument according with the present invention.

The flexible vinyl chloride resin laminate possessing the inner wall 2 and the outer surface layer 3 each of the compositions can be prepared by a multi-layer film molding device of common use. In the case of inflation molding, for example, a system provided with two extrusion molding machines 5, 6 and a multi-layer film die 4 as illustrated in FIG. 2 is employed. In this system, the components for the flexible vinyl chloride resin composition to form the inner wall 2 are supplied in predetermined mixing ratios through a hopper 8 of the second extrusion molding machine 6 and thoroughly melted and uniformly kneaded within a screw unit 10 and the resultant flexible vinyl chloride resin composition to form the inner wall 2 is extruded from the second extrusion molding machine 6 into a second flow tube 12 of the multi-layer film die 4. In the meantime, the components for the flexible vinyl chloride resin to form the outer wall 3 are similarly supplied in predetermined mixing ratios through a hopper 7 of the first extrusion molding machine 5 and thoroughly melted and uniformly kneaded within a screw unit 9 and the resultant flexible vinyl chloride resin to form the outer wall 3 is extruded from the first extrusion molding machine 5 into a first flow tube 11 of the multi-layer film die. The flexible vinyl chloride resin extruded into the first flow tube 11 and the vinyl chloride resin composition extruded into the second flow tube 12 are discharged respectively through an outer die lip 13 and an inner die lip 14 which both communicate with the flow tubes. The molten flexible vinyl chloride resin and the molden flexible vinyl chloride resin composition so discharged are fused to form a laminate. Further, the molten resin laminate so produced is discharged through the die 4 and, at the same time, inflated with the air blown in through an air blowing tube 15 and cooled and solidified on the outer surface with the air injected from a cooling ring (not shown). The vinyl chloride resin laminate 1 obtained after the cooling is lifted by nip rolls (not shown) and wound on a winding machine (not shown).

In the flexible vinyl chloride resin laminate 1 thus obtained, the layer destined to constitute the inner wall 2 has an embossed surface because of the prominence of cross-linked vinyl chloride resin particles contained in the layer and the layer destined to constitute the outer wall 3 has a smooth surface.

The method of this invention for the formation of the flexible vinyl chloride resin laminate 1 has been described above as effected by inflation molding. Also in the case of extrusion molding by the use of a T die or in the case of blow molding, a system similarly provided with two extrusion molding machines and a multi-layer die can be employed to obtain a flexible vinyl chloride laminate for forming the apparatus of this invention for medical treatment. In the flexible vinyl chloride resin laminate so obtained, the layer destined to constitute the inner wall of the medical instrument has a thickness in the range of 50 to 500 μm and the layer to constitute the outer layer has a thickness in the range of 500 to 50 μm. The ratio in thickness of the layer for the inner wall to the layer for the outer wall falls in the range of 1:1 to 1:10. On the inner wall surface are formed minute protuberances and depressions. The average of heights from tops to bottoms of the protuberances and depressions, namely the average height of the protuberances and depressions, falls in the range of 1 to 45 μm. When the flexible vinyl chloride resin forming the outer wall contains cross-linked vinyl chloride resin particles in less than 1.5% by weight, the outer wall surface also contains minute protuberances and depressions.

The apparatus of this invention for medical treatment is obtained by cutting, fabricating, and otherwise working in a desired shape the flexible vinyl chloride resin laminate produced as described above. When the medical instrument aimed at is in the form of a bag such as, for example, a bag for dialysis [represented by continuous ambulatory peritoneal dialysis (CAPD)], a bag for transfusion fluid, or a bag for blood, the vinyl chloride resin laminate obtained as described above it can be obtained by cutting two symmetrical pieces of prescribed shape from the vinyl chloride resin laminate, superposing the cut pieces one over the other attentively so that their inner and outer surfaces will fall on correct sides, and sealing the resulting envelope at prescribed positions.

When the medical instrument is in the form of a tube such as, for example, a plain tube, a connection tube, or an extension tube to be used in a transfusion set or a blood transfusion set, it can be obtained by molding the flexible vinyl chloirde resin laminate in the form of a tube of prescribed diameter from the beginning and cutting the produced tubular laminate in a prescribed length.

In the instrument of this invention, the inner wall is formed of the flexible vinyl chloride resin composition containing the cross-linked vinyl chloride resin particles described above. These cross-linked vinyl chloride resin particles serve to emboss the inner surface of the medical instrument. As the result, the opposed inner surfaces of the medical instrument are prevented from mutual blocking.

The medical instrument of this invention is subjected to sterilization prior to its use. Generally, this sterilization is carried out by autoclaving at about 121° C. for about 60 minutes. Even after the autoclaving sterilization performed at such a high temperature as this, the opposed inner surfaces of the apparatus do not yield to mutual blocking. Further, the medical instrument possesses transparency high enough for the fluid contained therein to be clearly seen through.

In the instrument of this invention, since the inner wall thereof is formed of the flexible vinyl chloride resin composition which contains the cross-linked vinyl chloride resin particles in a high concentration, the instrument is opaque when it is empty of its content such as transfusion fluid or blood. This medical instrument, when it is filled with its fluid, assumes transparency because the outer wall thereof is formed of the flexible vinyl chloride resin composition which has a very small cross-linked vinyl chloride resin particles content falling in the range of 0 to 1.5% by weight. The outer wall of the apparatus is such that possible blocking between the opposed outer surface of two adjoining apparatuses is avoided and desired visual inspection of the content of the instrument for detection of foreign matter and for determination of attributes such as color is attained easily and satisfactorily.

Now, one embodiment of the invention will be descirbed below with reference to the accompanying drawings. FIG. 3 illustrates a bag for holding a CAPD fluid. It comprises a bag body 20 having the inner surface of the flexible vinyl chloride resin laminate embossed with the cross-linked vinyl chloride resin particles, a fluid injection port 23a formed in the bag body 20, a communication mechanism 25 disposed on the bag body 20 interior side of the fluid injection port 23a and adapted to check the flow of the contained fluid and, when the bag is put to use, establish a path for the flow of the fluid, and a mixing injection port 24b. The bag body 20 is sealed along its peripheral edge 21 by a high-frequency welder. The fluid injection port 23a is provided with a communication tube 23 serving to guide the contained fluid of the bag body during its discharge from the bag body. This communication tube 23 is formed of the flexible vinyl chloride resin laminate which has the inner surface thereof embossed with cross-linked vinyl chloride resin particles. The communication mechanism 25 is composed of a tubular member 27 having an outside diameter virtually equal to the inside diameter of the fluid injection port 23a and a columnar member 26 disposed integrally at the leading end of the tubular member 27. These two members are both made of rigid plastic such as, for example, rigid vinyl chloride resin. A notch 28 is formed to intervene between the columnar member 26 and the tubular member 27. Before the bag is put to use, therefore, the columnar member checks the flow of the contained fluid of the bag. When the bag is put to use, communication is established between the interior 22 of the bag body and the communication tube 23 by bending the notch 28 of the communication mechanism 25 with finger tips and consequently severing th columnar member.

The mixing injection port 24b has the middle portion thereof barriered with a partition 29. It is provided at the leading end thereof with a rubber member 30 closed with a cover 31. A medicine desired to be added to the contained fluid of the bag can be introduced into the bag interior with a syringe pierced through the cover 31 and then the aforementioned partition 29. After the extraction of the syringe, the rubber member 30 serves to check the flow of the contained fluid.

Figure 5:
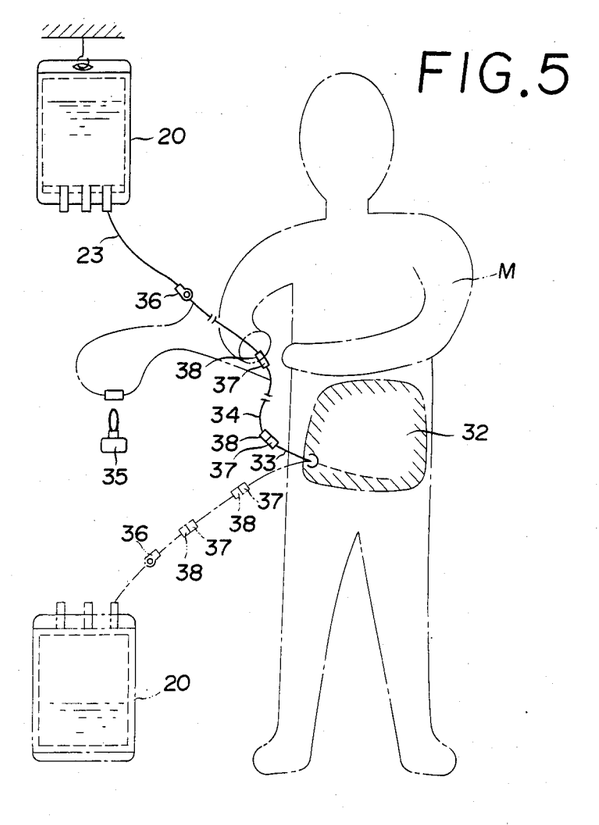
FIG. 5 is an artist's concept of the use of the CAPD bag.

Now, a typical application of the apparatus of this invention to continuous ambulatory peritoneal dialysis (CAPD). As illustrated in FIG. 5, a catheter 33 is surgically planted in the abdominal cavity 32 of a patient and a connector member 37 is fitted to the exposed end of the catheter 33. A tube 34 is prepared which has joined to the opposite ends thereof connector members 38, 37 sterilized in advance and covered each with a protective member. The connector members 38, 37 are stripped of the protective members and sterilized with the flame of an alcohol burner 15, for example. Then, the tube 34 is connected to the connector member 37 at the exposed end of the catheter. To the fluid injection port 23a of the bag body is joined a transfer tube 23 which has fitted to the free end thereof a connector member 38 sterilized in advance and covered with a protective member. The connector member 38 of the transfer tube 13 is stripped of the protective member and is joined to the connector member 37 of the tube 34 while being sterilized with the flame. Then, the bag body 20 is hung down at a position higher than the abdominal cavity of the patient and the communication mechanism 25 is opened by bending the notch 28 and breaking the columnar member 26 to establish a continuous path between the bag body and the catheter. The dialysis fluid is then injected into the abdominal cavity 32 by loosening a clamp 36. After the injection, the aforementioned clamp is closed and the tube 23 is coiled up and the bag body 20 is fastened to the waist of the patient's body. Then, the patient is free to walk and carry on his work. For the dialysis fluid now held inside the abdominal cavity 32 to be discharged after elapse of a fixed length of time, the patient is simply required to stretch the tube 23 and place the bag body 20 as on the floor. After the bag has served this purpose it can be replaced with a fresh supply after the connector members, 37, 38 have been disjoined while being sterilized with the flame.

Now, the present invention will be described more specifically below with reference to working examples.

EXAMPLES 1-4 AND CONTROLS 1-2

Varying compounds for first and second layers indicated in Table 1 were separately prepared and pelletized by the use of a Henschel mixer having an inner volume of 10 liters. The pelletized compounds consequently obtained were placed in an inflation molding system constructed as illustrated in FIG. 2, to produce an inflation molded laminate sheet having the second layer as an inner wall and a folding diameter of 100 mm and a thickness of 0.3 mm. The laminate sheet was cut into pieces 200 mm in length. The pieces were superposed one over the other and their joined edges were fused by high-frequency welding to complete a bag-shaped medical instrument. The medical instrument was tested as to the condition of mutual blocking of the opposed inner surfaces. The results are shown in Table 1. The condition of blocking observed was rated by a five-point scale to be defined below. The test for condition of blocking was also performed on the apparatus after sterilization by autoclaving.

0: Absolutely no blocking observed; a pinch at one end of sheet enables the bag to open naturally.
1: Partial blocking observed at points; the bag is easily opened.
2: Partial blocking observed at points; the bag is opened with difficulty.
3: Blocking observed throughout the entire inner surfaces; although the bag is opened with difficulty, the blocking is naturally solved when the bag is opened at the mouth.
4: Blocking observed throughout the entire inner surfaces; the bag is opened with difficulty and the blocking persists even after the bag is opened at the mouth.

The instrument, for the the determination of its transparency, was tested for absorbancy at 700 to 400 nm ($\log I_0/I$) under two conditions, one empty of fluid and the other full of the fluid. In all the samples, the difference of absorbancy in the spectrum range of 700 to 400 nm was not more than 0.05, denying the dependency of absorbancy upon wavelength. The results are shown in Table 1. The transparency in terms of absorbancy is rated by the following scale.

$>1.0$: White and opaque
0.5-1.0: White and translucent
$0.5>$: Colorless and transparent

TABLE 1

|  | Example 1 | | Example 2 | | Example 3 | | Example 4 | | Control 1 | Control 2 |
|---|---|---|---|---|---|---|---|---|---|---|
|  | First layer | Second layer | First layer | Second layer | First layer | Second layer | First layer | Second layer | Single layer | Single layer |
| Formulation |  |  |  |  |  |  |  |  |  |  |
| PCV (P = 1100) | 100 | 97 | 99 | 85 | 99 | 98.5 | 100 | 60 | 100 | 97 |
| Cross-linked PVC | — | 3 | 1 | 15 | 1 | 1.5 | — | 40 | — | 3 |
| DOP | 50 | 50 | 50 | 50 | 50 | 50 | 50 | 50 | 50 | 5 |
| Epoxidated soybean oil | 8 | 8 | 8 | 8 | 8 | 8 | 8 | 8 | 8 | 8 |
| Metallic soap | 1 | 1 | 1 | 1 | 1 | 1 | 1 | 1 | 1 | 1 |
| Lubricant | 2 | 2 | 2 | 2 | 2 | 2 | 2 | 2 | 2 | 2 |
| Blocking level |  |  |  |  |  |  |  |  |  |  |
| After molding and winding | 0 | | 0 | | 1 | | 0 | | 4 | 0 |
| After autoclaving sterilization | 0 | | 0 | | 0 | | 0 | | 4 | 0 |
| Absorbancy (max) |  |  |  |  |  |  |  |  |  |  |
| Empty of fluid | | 0.84 | | 0.92 | | 0.81 | | 1.50 | 0.24 | 1.55 |
| Full of fluid | | 0.22 | | 0.24 | | 0.23 | | 0.22 | 0.21 | 1.05 |

As described above, the medical instrument according to the present invention is an apparatus formed of a flexible vinyl chloride resin wall and therefore enabled to be flattened, which apparatus is characterized by the fact that the inner wall thereof whose opposed surfaces come into mutual contact when the apparatus is flattened is formed of a flexible vinyl chloride resin composition containing cross-linked vinyl chloride resin particles and, consequently, minute protuberances and depressions are formed in the aforementioned opposed surfaces of the inner wall. Thus, the opposed surfaces of the inner wall of the instrument are embossed and the possible blocking between the opposed inner surfaces of the instrument is precluded in spite of the fact that the apparatus is made of flexible vinyl chloride. This instrument, therefore, can be esily opened at the mouth and the entry of transfusion fluid, blood, etc. to the interior of the instrument can be attained smoothly. Since the instrument of this invention can have the inner surfaces thereof uniformly and easily embossed without necessitating any special device such as an embossing roll, it can be manufactured even by the heretofore impracticable inflation molding method. This instrument can also be manufactured in a tubular shape. Further, since the instrument of this invention does not develop the phenomenon of blocking between the opposed inner surfaces thereof even after it has been sterilized by autoclaving, it can be conveniently uilized in bags for holding transfusion fluid, blood, dialysis fluid, and particularly CAPD fluid. Moreover, since the instrument of this invention if formed of two layers, i.e. an inner wall and an outer wall, and the outer wall is made of a resin composition containing cross-linked vinyl chloride resin in a concentration in the range of 0 to 1.5% by weight, and, therefore, is possessed of a smooth surface, the apparatus, when filled with a fluid such as transfusion fluid or blood, exhibits high transparency and enables the contained fluid to be easily and perfectly inspected as to the attributes such as color and as to the presence of any foreign matter. Further in the instrument of the present invention, when the flexible vinyl chloride resin composition forming the inner wall of the apparatus contains the cross-linked vinyl chloride resin particles in a concentration falling in the range of 1.5 to 60% by weight, preferably 2 to 30% by weight, based on the total amount of vinyl chloride resin present in the flexible vinyl chloride resin composition, the preclusion of the phenomenon of blocking between the opposed inner surfaces of the apparatus can be attained most advantageously. This effect is highest when the average diameter of the partially cross-linked vinyl chloride resin particles falls in the range of 0.5 to 150 $\mu$m, preferably 1 to 100 $\mu$m.

The medical instrument according to this invention offers still better performance when the outer wall thereof is made of the flexible vinyl chloride resin composition containing less than 1.5% by weight of the cross-linked vinyl chloride resin, because the instrument is then free from the otherwise possible blocking between the opposed outer surfaces of two adjoining apparatuses.

What is claimed is:

1. A medical tubular instrument formed of a wall of flexible vinyl chloride resin and enabled to be flattened, which instrument is characterized by the fact that the inner wall thereof whose opposed surfaces come into mutual contact when said instrument is flattened is made of a flexible vinyl chloride resin composition containing cross-linked vinyl chloride resin particles and enabled to form minute protuberances and depressions in said inner wall surfaces, said cross-linked vinyl chloride resin particles having an average diameter of from 0.5 to 150 $\mu$m and being in a concentration of from 1.5 to 60% by weight based on the total amount of vinyl chloride resin present in said flexible vinyl chloride resin composition.

2. An instrument according to claim 1, wherein the outer wall thereof is a layer made of flexible vinyl chloride resin containing less than 1.5% by weight of cross-linked vinyl chloride resin particles.

3. An instrument according to claim 1, wherein said flexible vinyl chloride resin composition forming said inner wall contains said cross-linked vinyl chloride resin particles in a concentration falling in the range of 2 to 30% by weight based on the total amount of vinyl chloride resin present in said flexible vinyl chloride resin composition.

4. An instrument according to claim 1, wherein said cross-linked vinyl chloride resin particles are insoluble in tetrahydrofuran.

5. An instrument according to claim 1, wherein the thickness of said inner wall is in the range of about 50 to 500 $\mu$m and the thickness of said outer wall is in the range of about 50 to about 500 $\mu$m and the ratio in thickness of said inner wall to said outer wall is in the range of 1:1 to 1:10.

6. An instrument according to claim 1, wherein the average height of said protuberances and depressions is in the range of 1 to 45 $\mu$m.

7. An instrument according to claim 5, wherein minute protuberances and depressions are also formed in the surface of said outer wall.

8. An instrument according to claim 2, wherein said outer wall contains said cross-linked vinyl chloride resin particles in a concentration of not less than 0.01% by weight and less than 1.5% by weight.

9. An instrument according to claim 1, wherein the instrument is a bag.

10. An instrument according to claim 9, wherein the instrument is a bag holding therein dialysis fluid.

11. An instrument according to claim 9, wherein the instrument is a bag holding therein blood.

12. An instrument according to claim 9, wherein the instrument is a bag holding therein transfusion fluid.

13. An instrument according to claim 1, wherein the instrument is a tube.

14. An instrument according to claim 1, wherein the average diameter of said cross-linked vinyl chloride resin particles falls in the range of 1 to 100 $\mu$m.

15. An instrument acording to claim 1, wherein
the average diameter of said cross-linked vinyl chloride resin particles falls in the range of 1 to 100 $\mu$m;
said cross-linked vinyl chloride resin particles are in a concentration of from 2 to 30% by weight based on the total amount of vinyl chloride resin present in said flexible vinyl chloride resin composition;
the thickness of said inner wall is in the range of about 50 to 500 $\mu$m and the thickness of the outer wall is in the range of about 50 to about 500 $\mu$m and the ratio in thickness of said inner wall to said outer wall is in the range of 1:1 to 1:10;
the average height of said protuberances and depressions is in the range of 1 to 45 $\mu$m; and
said outer wall also contains said cross-linked vinyl chloride resin particles in a concentration of not less than 0.01% by weight and less than 1.5% by weight.

16. An instrument acording to claim 10, wherein
the average diameter of said cross-linked vinyl chloride resin particles falls in the range of 1 to 100 μm;
said cross-linked vinyl chloride resin particles are in a concentration of from 2 to 30% by weight based on the total amount of vinyl chloride resin present in said flexible vinyl chloride resin composition;
the thickness of said inner wall is in the range of about 50 to 500 μm and the thickness of the outer wall is in the range of about 50 to about 500 μm and the ratio in thickness of said inner wall to said outer wall is in the range of 1:1 to 1:10;
the average height of said protuberances and depressions is in the range of 1 to 45 μm; and
said outer wall also contains said cross-linked vinyl chloride resin particles in a concentration of not less than 0.01% by weight and less than 1.5% by weight.

17. An instrument acording to claim 11, wherein
the average diameter of said cross-linked vinyl chloride resin particles falls in the range of 1 to 100 μm;
said cross-linked vinyl chloride resin particles are in a concentration of from 2 to 30% by weight based on the total amount of vinyl chloride resin present in said flexible vinyl chloride resin composition;
the thickness of said inner wall is in the range of about 50 to 500 μm and the thickness of the outer wall is in the range of about 50 to about 500 μm and the ratio in thickness of said inner wall to said outer wall is in the range of 1:1 to 1:10;
the average height of said protuberances and depressions is in the range of 1 to 45 μm; and
said outer wall also contains said cross-linked vinyl chloride resin particles in a concentration of not less than 0.01% by weight and less than 1.5% by weight.

* * * * *

UNITED STATES PATENT AND TRADEMARK OFFICE
CERTIFICATE OF CORRECTION

PATENT NO. : 4,657,541
DATED : April 14, 1987
INVENTOR(S) : ICHIKAWA et al

It is certified that error appears in the above-identified patent and that said Letters Patent is hereby corrected as shown below:

Column 1, line 67, change "along" to --alone--.

Column 2, line 36, change "surface" to --surfaces--.

Column 9, line 23, change "burner 15" to --burner 35--.

Column 9, line 30, change "tube 13" to --tube 23--.

Column 11, line 16, change "esily" to --easily--.

Column 11, line 31, change "if" to --is--.

Signed and Sealed this

Ninth Day of February, 1993

Attest:

STEPHEN G. KUNIN

*Attesting Officer*

*Acting Commissioner of Patents and Trademarks*